US006554811B2

(12) United States Patent
Barth

(10) Patent No.: US 6,554,811 B2

(45) Date of Patent: Apr. 29, 2003

(54) INTERNAL ARTIFICIAL VAGINA FOR COLLECTING ANIMAL SEMEN

(75) Inventor: Albert D. Barth, Saskatoon (CA)

(73) Assignee: University of Saskatchewan Technologies Inc., Saskatoon (CA)

(*) Notice: Subject to any disclaimer, the term of this patent is extended or adjusted under 35 U.S.C. 154(b) by 0 days.

(21) Appl. No.: 09/945,690

(22) Filed: Sep. 5, 2001

(65) Prior Publication Data

US 2002/0032419 A1 Mar. 14, 2002

Related U.S. Application Data

(60) Provisional application No. 60/231,326, filed on Sep. 8, 2000.

(51) Int. Cl.[7] ........................ A61F 5/453

(52) U.S. Cl. ........................ 604/349; 600/40; 128/830

(58) Field of Search ........................ 604/327, 330, 604/346, 347, 349–353, 906; 600/33, 35, 38–41; 128/830, 839–841, 834–837

(56) References Cited

U.S. PATENT DOCUMENTS

| | | | | | |
|---|---|---|---|---|---|
| 3,309,791 | A | * | 3/1967 | Kelley et al. | 434/225 |
| 3,547,102 | A | * | 12/1970 | Frenkel | 600/575 |
| 4,312,350 | A | | 1/1982 | Doan | |
| 4,620,531 | A | * | 11/1986 | Dyer | 604/349 |
| 4,690,678 | A | | 9/1987 | Douglas-Hamilton | |
| 4,744,352 | A | | 5/1988 | Emery | |
| D330,762 | S | * | 11/1992 | Anderson et al. | D24/108 |
| 5,437,652 | A | * | 8/1995 | Anatolievich | 604/349 |
| 5,458,559 | A | | 10/1995 | Gauntlett | |
| 5,540,670 | A | | 7/1996 | Lindholm-Ventola | |
| 5,685,871 | A | * | 11/1997 | Lindholm-Ventola | 604/349 |
| 5,695,446 | A | * | 12/1997 | Lindholm-Ventola | 600/38 |
| 5,961,503 | A | * | 10/1999 | Simmet et al. | 604/349 |
| 6,035,853 | A | * | 3/2000 | Alla et al. | 128/830 |
| 6,059,716 | A | * | 5/2000 | Lee et al. | 600/35 |
| 6,071,231 | A | * | 6/2000 | Mendoza et al. | 600/35 |
| 6,071,689 | A | * | 6/2000 | Seidel et al. | 435/2 |
| 6,090,088 | A | * | 7/2000 | Nichols | 604/347 |
| 6,149,579 | A | * | 11/2000 | Lee | 600/35 |

FOREIGN PATENT DOCUMENTS

| | | | | |
|---|---|---|---|---|
| WO | WO 93/02634 | * | 2/1993 | A61D/19/02 |
| WO | WO 93/18730 | * | 9/1993 | A61F/19/02 |
| WO | WO 93/18731 | * | 9/1993 | A61F/19/02 |

* cited by examiner

*Primary Examiner*—Weilun Lo
*Assistant Examiner*—Michael G. Bogart

(57) ABSTRACT

An internal artificial vagina for collecting animal semen including a stiff support frame comprising a straight bar portion having at one end thereof a generally circular ring portion substantially perpendicular to the axis of the bar portion and an attachment means at the other end of the bar portion. An elastomeric tube open at both ends is adapted to slide within the frame ring portion with an end portion of the elastomeric tube stretched and pulled outwardly around the frame ring portion whereby the ring portion is retained within the folded portion of the elastomeric tube. The other end portion of the elastomeric tube is fixed to the attachment means of the frame. A replaceable semen collection bag is also provided in the form of an elongated generally cylindrical thin, flexible plastic member having a closed end and an open end. The collection bag is adapted to slide over the elastomeric tube with the open end being detachably connected to the elastomeric tube and the collection bag having a length substantially greater than the length of the elastomeric tube.

7 Claims, 2 Drawing Sheets

INTERNAL ARTIFICIAL VAGINA FOR COLLECTING ANIMAL SEMEN

This invention relates to a method and apparatus for collecting seminal fluids and, more particularly, to an internal artificial vagina for collecting semen from animals. It claims the benefit of U.S. Provisional Application Ser. No. 60/231,326, filed Sep. 8, 2000.

FIELD OF THE INVENTION

BACKGROUND OF THE INVENTION

Artificial insemination is widely used in modern animal breeding, e.g. in the breeding of cows and zoo animals. The most common method of collecting semen in animals is by the use of an artificial vagina. Many different types of these artificial vaginas have been developed such as those described in U.S. Pat. Nos. 4,312,350; 4,690,678 and 5,540,670. Some of these can become quite elaborate such as that described in U.S. Pat. No. 4,312,350 and may include a dummy animal as shown in U.S. Pat. No. 5,540,670.

It is an object of the present invention to develop an artificial vagina which can be used internally in a female animal.

SUMMARY OF THE INVENTION

The present invention in its broadest aspect relates to an internal artificial vagina for collecting animal semen, particularly bovine semen. It includes a stiff support frame comprising a straight bar portion having at one end thereof a generally circular ring portion substantially perpendicular to the axis of the bar portion and an attachment means at the other end of the bar portion. An elastomeric tube open at both ends is adapted to slide within the frame ring portion with an end portion of the elastomeric tube stretched and pulled outwardly around the frame ring portion whereby the ring portion is retained within the folded portion of the elastomeric tube. The other end portion of the elastomeric tube is fixed to the attachment means of the frame. A replaceable semen collection bag is also provided comprising an elongated generally cylindrical thin, flexible plastic member having a closed end and an open end. The collection bag is adapted to slide over the elastomeric tube with the open end being detachably connected to the elastomeric tube and the collection bag having a length substantially greater than the length of the elastomeric tube.

The stiff support frame may be in a form of plastic coated wire or a strong polymeric material. The attachment means on the frame may conveniently be in the form of a small loop which can then be used for stitching the frame to the elastomeric tube.

The semen collection bag typically has the closed end thereof tapered to form a point. This collection bag is intended to be disposable and may be fixed to the elastomeric tube by means of adhesive tape.

While the invention is described hereinafter with respect to the collection of bull semen, it is equally useful for collecting semen from a wide variety of animals. For instance, it may be used in the artificial insemination of zoo animals as well as native animals such as deer, elk, moose, etc.

BRIEF DESCRIPTION OF THE DRAWINGS

An embodiment of the invention will now be described by way of example only, with reference to the accompanying drawings, in which:

As seen in FIG. 1, the support frame 10 includes a straight bar or rod portion 11 having at one end thereof a generally circular ring portion 12 which is substantially perpendicular to the axis of the rod portion 11. At the other end of the rod portion 11 is an attachment means 13 preferably in the form of a small loop.

According to a preferred feature the bar or rod 11 is telescopic so that its length is adjustable. For this purpose the rod 11 may be split in the middle of its length into two parts. These two rod parts then slide within a sleeve, thereby permitting adjustment of the length of support frame 10. The portions of the rod 11 that move within this sleeve may be serrated so that the length of the frame 10 will remain friction fixed while in use.

Figure 1:
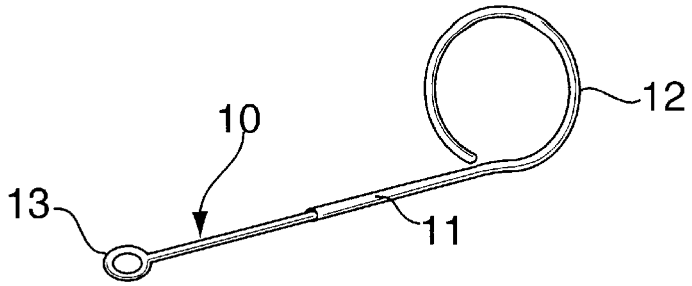
FIG. 1 shows a support frame according to the invention.
Figure 2:
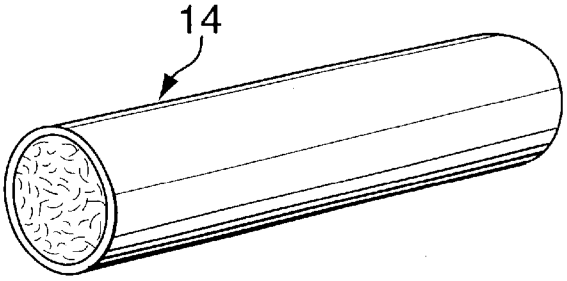
FIG. 2 shows an elastomeric tube portion of the assembly.
Figure 3:
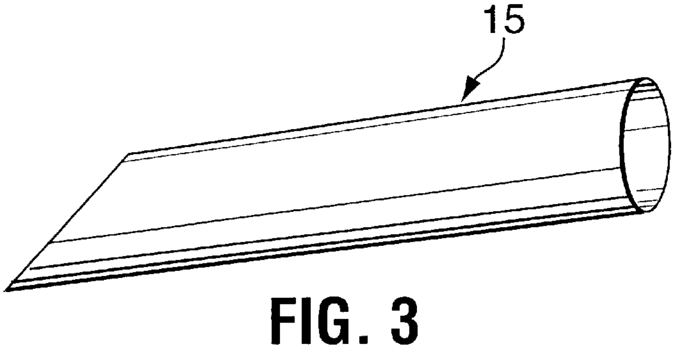
FIG. 3 shows a semen collection bag.
Figure 4:
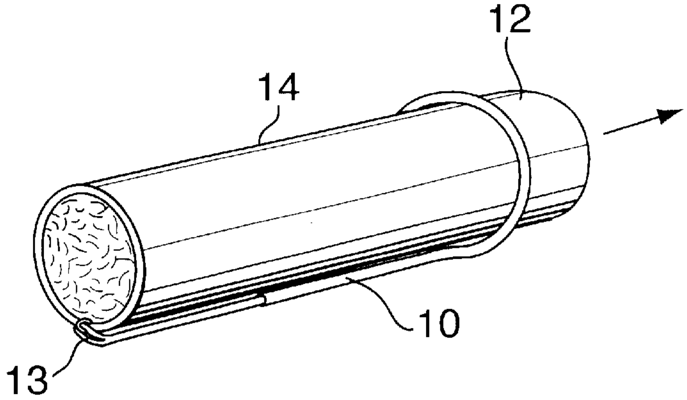
FIG. 4 shows the frame and elastomeric tube being assembled.
Figure 5:
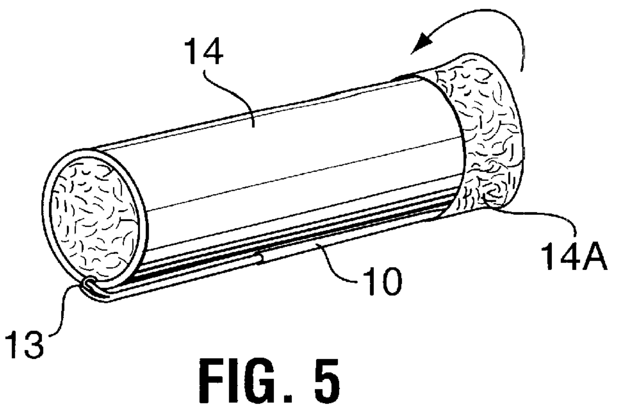
FIG. 5 shows further of the frame and elastomeric tube assembly.

The elastomeric tube 14 is preferably formed of a relatively thick wall rubber tube typically having a textured inner surface. This tube and the frame 10 form an assembly as shown in FIGS. 4 and 5. Thus, one end of tube 14 is slide through the loop 12 so that a portion projects beyond the loop as shown in FIG. 4. This projecting portion is then stretched and folded back over the loop to provide a folded back portion **14*a*. This folded over portion 14*a* provides a relatively soft resilient entry area for the artificial vagina. The opposite open end of the tube 14 is attached to the small loop 13** of the frame, e.g. by means of stitching.

Figure 6:
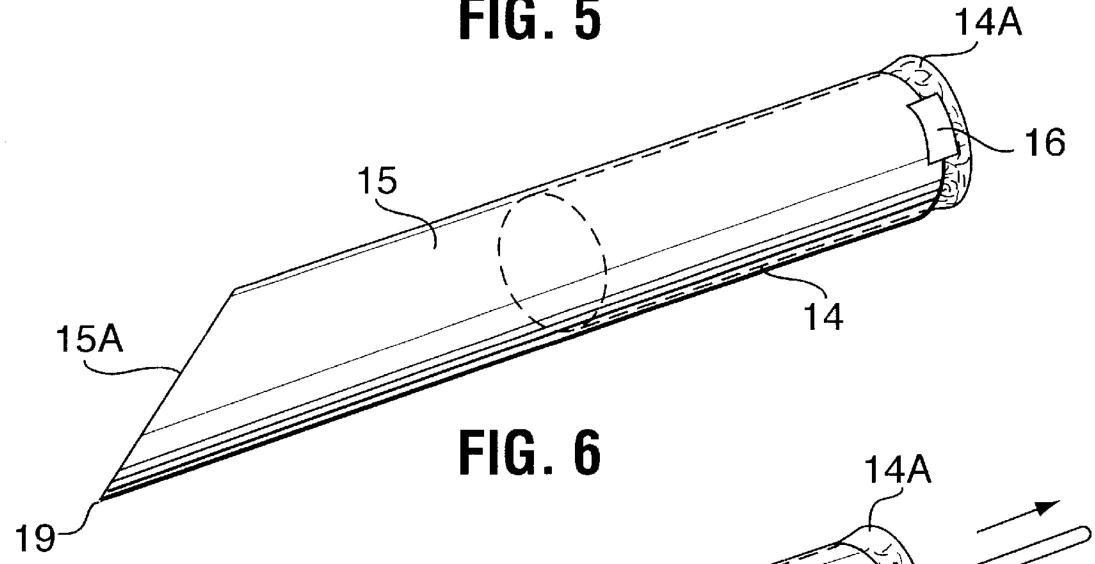
FIG. 6 shows the installation of the semen collection bag.

For use in collecting semen, a semen collection bag 15 is provided. This is in the form of a relatively long thin wall plastic tube having a tapered closed end **15*a* terminating in a point 19. The open end of the collection bag is slid over the elastomeric tube 14 as shown in FIG. 6 and is attached thereto by means of adhesive strips 16**.

Figure 7:
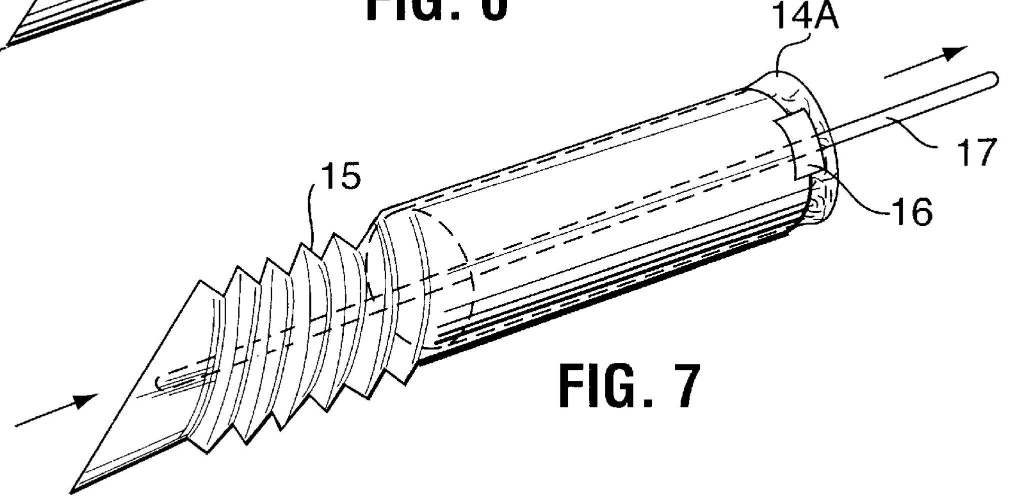
FIG. 7 shows the assembly with the semen collection bag being folded.
Figure 8:
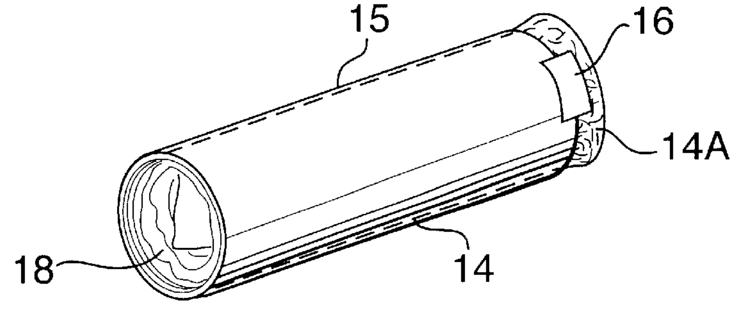
FIG. 8 shows the complete assembly ready for use.

For use, it is preferred that the semen collection bag be folded in an accordion-like fashion and stuffed into the end of the artificial vagina tube 14. This folding action may conveniently be performed by placing a rod 17 through the artificial vagina up to the end of the collection bag and then sliding the bag down the rod as it is withdrawn from the artificial vagina. This folding action is shown in FIG. 7 and the complete assembly ready for use with the collection bag folded and stuffed into the end of the artificial vagina is shown in FIG. 8.

For use, the anterior 75% of the artificial vagina is preferably wetted with saline and the posterior 25% is preferably lightly coated with a nonspermacidal lubricant. The mouth of the artificial vagina is also well lubricated. Some lubricant may be also placed on the outside of the artificial vagina so that it slides into the cow more easily. The long bar 10 of the frame stays ventrally oriented inside the cow and the small loop 13 goes up to the cervix. The ring end 12, **14*a*** of the artificial vagina goes just inside the vestibular sphincter, i.e. about 6 cm into the cow. When the artificial vagina is in place, it can not be seen from the outside.

When the bull serves the cow, the accordion folded portion of the bag 15 is pushed out by the bull's penis and he ejaculates into the lower end of the bag. After the bull has served the cow, the artificial vagina is pulled out, the tip 19 is cut off the bag and the semen is drained into a test tube.

The collection bag is then removed from the artificial vagina, a fresh collection bag is attached in the same manner as described above and the procedure is repeated.

The elastomeric tube and frame assembly can be reused innumerable times and only the semen collection bag needs replacement. The artificial vagina should be stored in darkness, as light tends to cause deterioration of the rubber.

Obviously, many modifications and variations of the present invention are possible in light of the above teachings. For instance its dimensions can vary depending on the animals for which it is to be used. For collecting bull semen, the frame ring portion has a diameter of about 50 to 75 mm, the frame has a total length of about 20 to 25 cm and the collection bag has a total length of about 45 to 60 cm. It is therefore to be understood that, within the scope of the appended claims, the invention may be practiced otherwise than as specifically described.

What is claimed is:

1. An internal artificial vagina for collecting animal semen comprising:

(a) a stiff support frame comprising a straight bar portion having at one end thereof of a generally circular ring portion substantially perpendicular to the axis of said bar portion and an attachment means at the other end of said bar portion;

(b) an elastomeric tube open at both ends adapted to slide within said frame ring portion with an end portion stretched and folded outwardly around the frame ring portion whereby the ring portion is retained within the folded portion of the elastomeric tube and the other end portion of the elastomeric tube being fixed to said attachment means of the frame; and (c) a replaceable semen collection bag comprising an elongated generally cylindrical thin, flexible plastic member having a closed end and an open end, said collection bag being adapted to slide over the elastomeric tube with the open end thereof being detachably connected to the elastomeric tube and said collection bag having a length substantially greater than the length of the elastomeric tube.

2. The internal artificial vagina as claimed in claim 1 wherein the attachment means of said frame comprises a small loop for stitching the frame to the elastomeric tube.

3. The internal artificial vagina as claimed in claim 1 wherein the elastomeric tube is a rubber tube with a textured inner surface.

4. The internal artificial vagina as claimed in claim 1 wherein the closed end of the semen collection bag is tapered to form a point.

5. The internal artificial vagina as claimed in claim 1 wherein the stiff support frame comprises a plastic coated wire.

6. The internal artificial vagina as claimed in claim 1 wherein the semen collection bag is fixed to the elastomeric tube by means of adhesive tape.

7. The internal artificial vagina as claimed in claim 1 for collecting bull semen wherein the frame ring portion has a diameter of about 50 to 75 mm, the frame has a total length of about 20 to 25 cm and the collection bag has a total length of about 45 to 60 cm.

* * * * *